(12) United States Patent
Alig et al.

(10) Patent No.: US 6,255,328 B1
(45) Date of Patent: *Jul. 3, 2001

(54) SUBSTITUTED THIAZOLINES AND THEIR USE FOR CONTROLLING ANIMAL PESTS

(75) Inventors: Bernd Alig, Königswinter; Udo Kraatz, Leverkusen; Wolfgang Krämer, Burscheid; Reinhard Lantzsch, Wuppertal; Albrecht Marhold, Leverkusen; Christoph Erdelen, Leichlingen; Ulrike Wachendorff-Neumann, Neuwied; Andreas Turberg, Haan; Norbert Mencke, Leverkusen, all of (DE)

(73) Assignee: Bayer Aktiengesellschaft, Leverkusen (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/091,768
(22) PCT Filed: Dec. 10, 1996
(86) PCT No.: PCT/EP96/05505
§ 371 Date: Jun. 19, 1998
§ 102(e) Date: Jun. 19, 1998
(87) PCT Pub. No.: WO97/23468
PCT Pub. Date: Jul. 3, 1997

(30) Foreign Application Priority Data

Dec. 22, 1995 (DE) .............................. 195 48 419

(51) Int. Cl.$^7$ .................... C07D 277/10; A01N 43/78
(52) U.S. Cl. ............................... 514/365; 548/146
(58) Field of Search ............... 548/146; 514/365

(56) References Cited

U.S. PATENT DOCUMENTS 5,578,625 * 11/1996 Suzuki ............................. 514/374

FOREIGN PATENT DOCUMENTS

| 0 345 775 | 12/1989 | (EP) . |
| 0 432 661 | 6/1991 | (EP) . |
| 0 645 085 | 3/1995 | (EP) . |
| WO 95/04726 | 2/1995 | (WO) . |
| WO 96/40659 | 12/1996 | (WO) . |

OTHER PUBLICATIONS

Chemical Abstracts, vol. 124, No. 23, Abstract No. 317137g, Jun. 3, 1996.
Journal of The Chemical Society, Sec. C., Organic Chemistry, 1969 pp. 1120–1122, "The Circular Dichriosmof N–thiobenzoyl–L–alpha–amino–acids".

* cited by examiner

Primary Examiner—Robert Gerstl
(74) Attorney, Agent, or Firm—Norris, McLaughlin & Marcus, P.A.

(57) ABSTRACT

The invention relates to novel substituted thiazolines of the formula (I)

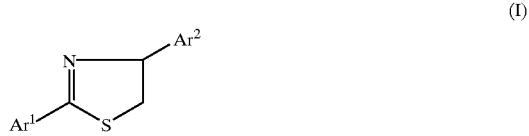

in which
Ar$^1$ and Ar$^2$ each represent independently of one another optionally substituted phenyl,
processes for their preparation, and their use for controlling animal pests.

12 Claims, No Drawings

SUBSTITUTED THIAZOLINES AND THEIR USE FOR CONTROLLING ANIMAL PESTS

The invention relates to novel substituted thiazolines, processes for their preparation, and to their use for controlling animal pests.

It is already known that certain oxazoline derivatives have insecticidal and acaricidal properties (cf. for example EP-A-0 345 775 or EP-A-0 432 661).

However, the potency and/or persistency of these prior-art compounds is not entirely satisfactory in all fields of application, in particular when used against certain organisms or at low application rates.

The invention provides novel substituted thiazolines of the formula (I)

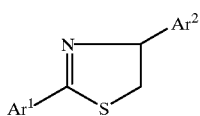

(I)

in which
Ar$^1$ and Ar$^2$ each represent independently of one another optionally substituted phenyl.

The invention further provides a process for preparing the novel substituted thiazolines of the formula (I) by reacting
a) oxazolines of the formula (II)

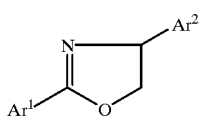

(II)

in which
Ar$^1$ and Ar$^2$ each have the abovementioned meaning with a sulphurizing agent, optionally in the presence of a diluent;
or by reacting
b) thiazolines of the formula (Ia)

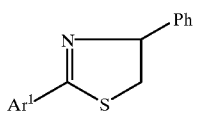

(Ia)

in which
Ar$^1$ has the abovementioned meaning and
Ph represents optionally substituted halogenophenyl
with boronic acids of the formula (III)

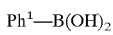

Ph$^1$—B(OH)$_2$    (III)

in which
Ph$^1$ represents optionally substituted phenyl
in the presence of a base, optionally in the presence of a catalyst and in the presence of a diluent.

Furthermore, it has been found that the novel substituted thiazolines of the formula (I) are highly suitable for controlling animal pests, in particular insects, arachnids and nematodes, encountered in agriculture, in forestry, in the protection of stored products and of materials, and in the hygiene field.

Surprisingly, the substituted thiazolines of the formula (I) according to the invention have a considerably higher activity against animal pests than the prior-art compounds of a similar structure.

Formula (I) provides a general definition of the compounds according to the invention.

Preferred substituents or ranges of the radicals mentioned in the formulae given hereinabove and hereinbelow are illustrated below.

Ar$^1$ preferably represents phenyl which is optionally substituted by one to five identical or different substituents from the group consisting of:
halogen, nitro, cyano, hydroxyl, amino,
$C_1$–$C_6$-alkyl,
$C_1$–$C_6$-alkoxy,
$C_1$–$C_6$-alkylthio,
$C_1$–$C_6$-alkylsulphinyl,
$C_1$–$C_6$-alkylsulphonyl,
$C_1$–$C_6$-halogenoalkyl,
$C_1$–$C_6$-halogenoalkoxy,
$C_1$–$C_6$-halogenoalkylthio,
$C_1$–$C_6$-halogenoalkylsulphinyl,
$C_1$–$C_6$-halogenoalkylsulphonyl,
$C_1$–$C_6$-alkoxy-$C_1$–$C_6$-alkyl,
$C_1$–$C_6$-alkylamino,
di-($C_1$–$C_6$-alkyl)-amino,
and phenyl, benzyl, benzyloxy, phenethyl, phenethenyl, phenethinyl, phenoxy or phenylthio, each of which is optionally substituted in particular in the phenyl moiety by one to five identical or different substituents from the group consisting of halogen, $C_1$–$C_4$-alkyl, $C_1$–$C_4$-halogenoalkyl, $C_1$–$C_4$-alkoxy, $C_1$–$C_4$-halogenoalkoxy, $C_1$–$C_4$-alkylthio or $C_1$–$C_4$-halogenoalkylthio.

Ar$^2$ preferably represents phenyl which is optionally substituted by one to five identical or different substituents from the group consisting of:
halogen,
$C_1$–$C_{18}$-alkyl,
$C_1$–$C_8$-alkoxy-$C_1$–$C_8$-alkyl,
$C_1$–$C_8$-halogenoalkoxy,
$C_1$–$C_4$-halogenoalkyl,
$C_1$–$C_{18}$-alkoxy which is optionally interrupted by a further 1 to 3 oxygen atoms,
$C_1$–$C_{18}$-alkylthio,
$C_1$–$C_8$-halogenoalkylthio,
tri-$C_1$–$C_8$-alkylsilyl,
phenyl-di-$C_1$–$C_8$-alkylsilyl,
3,4-difluoromethylenedioxo,
3,4-tetrafluoroethylenedioxo,
a benzo-fused group,
a fused $C_4$-alkanediyl group,
benzyliminooxymethyl which is optionally substituted by $C_1$–$C_4$-alkyl, $C_3$–$C_6$-cycloalkyl or halogen,
cyclohexyl or cyclohexyloxy, each of which is optionally substituted by $C_1$–$C_6$-alkyl, $C_1$–$C_6$-alkoxy, cyclohexyl or phenyl,
pyridyloxy which is optionally mono- or disubstituted by identical or different substituents from the group consisting of halogen, $C_1$–$C_4$-alkyl or $C_1$–$C_4$-halogenoalkyl,
and phenyl, phenyl-$C_1$–$C_6$-alkyl, phenethenyl, phenethinyl, phenoxy, phenylthio, phenyl-$C_1$–$C_6$- alkyloxy or benzylthio, each of which is optionally substituted in particular in the phenyl moiety by one to three identical or different $R^1$ and/or optionally substituted in particular in the phenyl moiety by one or two identical or different —$OR^2$.

$R^1$ preferably represents halogen, $C_1$–$C_6$-alkyl or $C_1$–$C_6$-alkoxy.

$R^2$ preferably represents hydrogen, or $C_1$–$C_{12}$-alkyl, $C_3$–$C_{12}$-alkenyl, or $C_3$–$C_{12}$-alkinyl, or $C_1$–$C_6$-halogenoalkyl having one or more fluorine and/or chlorine atoms, or $C_3$–$C_6$-cycloalkyl or $C_3$–$C_6$-cycloalkyl-$C_1$–$C_4$-alkyl, each of which is optionally mono- or polysubstituted in the cycloalkyl moiety by identical or different substituents from the group consisting of:

halogen, $C_1$–$C_4$-alkyl, $C_2$–$C_4$-alkenyl which is optionally mono- or polysubstituted by halogen, and phenyl or styryl, each of which is optionally mono- or polysubstituted, in particular in the phenyl moiety, by halogen;

or represents $C_4$–$C_6$-cycloalkenyl or $C_4$–$C_6$-cycloalkenyl-$C_1$–$C_4$-alkyl, each of which is optionally mono- or polysubstituted by identical or different halogen and/or $C_1$–$C_4$-alkyl substituents;

or represents phenyl-$C_1$–$C_4$-alkyl or naphthylmethyl, each of which is optionally mono- or polysubstituted in the aryl moiety by identical or different substituents from the group consisting of:

halogen, $C_1$–$C_{12}$-alkyl, $C_1$–$C_{12}$-halogenoalkyl having one or more fluorine and/or chlorine atoms, $C_1$–$C_{12}$-alkoxy and $C_1$–$C_{12}$-halogenoalkoxy having one or more fluorine and/or chlorine atoms;

or represents the radical —$COR^3$.

$R^3$ preferably represents $C_1$–$C_{12}$-alkyl, or $C_1$–$C_{12}$-alkoxy, or $C_3$–$C_{12}$-alkenyl, or $C_3$–$C_{12}$-alkenyloxy, or represents $C_3$–$C_6$-cycloalkyl, $C_3$–$C_{10}$-cycloalkyloxy or $C_3$–$C_{10}$-cycloalkyl-$C_1$–$C_6$-alkoxy, each of which is optionally mono- or polysubstituted in the cycloalkyl moiety by identical or different substituents from the group consisting of:

$C_1$–$C_4$-alkyl, halogen, $C_1$–$C_4$-halogenoalkyl having one or more fluorine and/or chlorine atoms and $C_2$–$C_4$-halogenoalkenyl having one or more fluorine and/or chlorine atoms;

or represents phenyl or naphthyl, each of which is optionally mono- or polysubstituted by identical or different substituents from the group consisting of:

halogen, $C_1$–$C_{12}$-alkyl, $C_1$–$C_{12}$-halogenoalkyl having one or more fluorine and/or chlorine atoms, $C_1$–$C_{12}$-alkoxy and $C_1$–$C_{12}$-halogenoalkoxy having one or more fluorine and/or chlorine atoms;

or represents the radical —NR—$R^5$.

$R^4$ preferably represents hydrogen or $C_1$–$C_{12}$-alkyl.

$R^5$ preferably represents $C_1$–$C_{12}$-alkyl, $C_1$–$C_{12}$-halogenoalkyl having one or more fluorine and/or chlorine atoms, or $C_3$–$C_6$-cycloalkyl or $C_3$–$C_6$-cycloalkyl-$C_1$–$C_4$-alkyl, each of which is optionally mono- or polysubstituted in the cycloalkyl moiety by identical or different substituents from the group consisting of:

$C_1$–$C_4$-alkyl, halogen, $C_1$–$C_4$-halogenoalkyl having one or more fluorine and/or chlorine atoms and $C_2$–$C_4$-halogenoalkenyl having one or more fluorine and/or chlorine atoms;

or represents phenyl or phenyl-$C_1$–$C_6$-alkyl, each of which is optionally mono- or polysubstituted, in particular in the phenyl moiety, by identical or different substituents from the group consisting of:

halogen, $C_1$–$C_{12}$-alkyl, $C_1$–$C_{12}$-halogenoalkyl having one or more fluorine and/or chlorine atoms, $C_1$–$C_{12}$-alkoxy and $C_1$–$C_{12}$-halogenoalkoxy having one or more fluorine and/or chlorine atoms;

or represents the radical —$C(R^6R^7)$—$C(R^8)$=$NOR^9$.

$R^6$ and $R^7$ are identical or different and preferably represent hydrogen or $C_1$–$C_4$-alkyl.

$R^8$ preferably represents hydrogen, $C_1$–$C_4$-alkyl or $C_3$–$C_6$-cycloalkyl which is optionally mono-, di- or trisubstituted by identical or different substituents from the group consisting of $C_1$–$C_4$-alkyl, halogen or $C_1$–$C_4$-halogenoalkyl.

$R^9$ preferably represents $C_1$–$C_4$-alkyl.

$Ar^1$ particularly preferably represents phenyl which is optionally substituted by one to five, in particular one to three, identical or different substituents from the group consisting of:

F, Cl, Br, nitro, cyano, hydroxyl, amino, $C_1$–$C_4$-alkyl, $C_1$–$C_4$-alkoxy, $C_1$–$C_4$-alkylthio, $C_1$–$C_4$-alkylsulphinyl, $C_1$–$C_4$-alkylsulphonyl, $C_1$–$C_4$-halogenoalkyl, $C_1$–$C_4$-halogenoalkoxy, $C_1$–$C_4$-halogenoalkylthio, $C_1$–$C_4$-halogenoalkylsulphinyl, $C_1$–$C_4$-halogenoalkylsulphonyl, $C_1$–$C_4$-alkylamino, di-($C_1$–$C_4$-alkyl)-amino, and phenyl which is optionally substituted by one to three identical or different substituents from the group consisting of F, Cl, Br, $C_1$–$C_4$-alkyl, $C_1$–$C_4$-alkyl which is substituted by one to six identical or different substituents from the group consisting of F and Cl, $C_1$–$C_4$-alkoxy, $C_1$–$C_4$-alkoxy which is substituted by one to six identical or different substituents from the group consisting of F and Cl, $C_1$–$C_4$-alkylthio and $C_1$–$C_4$-alkylthio which is substituted by one to six identical or different substituents from the group consisting of F and Cl.

$Ar^2$ particularly preferably represents phenyl which is optionally substituted by one to five, in particular one to three, identical or different substituents from the group consisting of:

F, Cl, Br, $C_1$–$C_{18}$-alkyl, $C_1$–$C_6$-alkoxy-$C_1$–$C_8$-alkyl, $C_1$–$C_6$-alkoxy which is substituted by one to six identical or different substituents from the group consisting of F and Cl, $C_1$–$C_2$-alkyl which is substituted by one to five identical or different substituents from the group consisting of F and Cl, $C_1$–$C_{18}$-alkoxy and —$(OC_2H_4)_{1-3}$—O—$C_1$–$C_6$-alkyl, $C_1$–$C_{15}$-alkylthio, $C_1$–$C_8$-alkylthio which is substituted by one to six identical or different substituents from the group consisting of F and Cl, tri-$C_1$–$C_6$-alkylsilyl, phenyl-di-$C_1$–$C_6$-alkylsilyl, 3,4-difluoromethylenedioxo,
3,4-tetrafluoroethylenedioxo,
a benzo-fused group,
a fused $C_4$-alkanediyl group,
the groupings

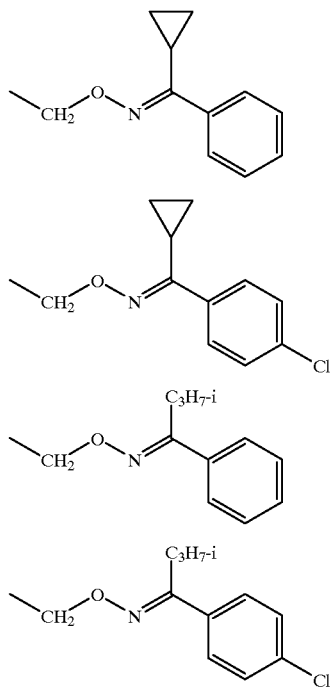

cyclohexyl or cyclohexyloxy, each of which is optionally substituted by $C_1$–$C_4$-alkyl, $C_1$–$C_4$-alkoxy, cyclohexyl or phenyl,
pyridyloxy which is optionally substituted by one or two identical or different substituents from the group consisting of F, Cl or $CF_3$,
and phenyl which is optionally substituted by one to three identical or different $R^1$ radicals and/or optionally substituted by one or two identical or different —$OR^2$ groupings.

$R^1$ particularly preferably represents fluorine, chlorine or bromine.

$R^2$ particularly preferably represents hydrogen, or $C_1$–$C_6$-alkyl, or $C_3$–$C_{12}$-alkenyl, or $C_3$–$C_6$-alkinyl, $C_1$–$C_4$-halogenoalkyl having two or more fluorine and/or chlorine atoms, or $C_3$–$C_6$-cycloalkyl or $C_3$–$C_6$-cycloalkyl-$C_1$–$C_4$-alkyl, each of which is optionally mono- or polysubstituted in the cycloalkyl moiety by identical or different substituents from the group consisting of:
fluorine, chlorine, bromine, $C_1$–$C_2$-alkyl, $C_2$–$C_3$-alkenyl which is optionally mono- or polysubstituted by fluorine and/or chlorine and phenyl and styryl, each of which is optionally mono- or polysubstituted in particular in the phenyl moiety by fluorine and/or chlorine,
and $C_4$–$C_6$-cycloalkenyl and $C_4$–$C_6$-cycloalkenylmethyl, each of which is optionally mono- or polysubstituted by identical or different substituents from the group consisting of fluorine and chlorine,
and phenyl-$C_1$–$C_4$-alkyl which is optionally mono- or polysubstituted in the phenyl moiety by identical or different substituents from the group consisting of:
fluorine, chlorine, $C_1$–$C_4$-alkyl, halogenomethyl having one or more fluorine and/or chlorine atoms, $C_1$–$C_4$-alkoxy and $C_1$–$C_4$-halogenoalkoxy having one or more fluorine and/or chlorine atoms, and the radical —$COR^3$.

$R^3$ particularly preferably represents $C_1$–$C_4$-alkyl, or $C_1$–$C_4$-alkoxy, or $C_3$–$C_6$-alkenyl, or $C_3$–$C_6$-alkenyloxy, or $C_3$–$C_6$-cycloalkyl, $C_3$–$C_6$-cycloalkyloxy or $C_3$–$C_6$-cycloalkyl-$C_1$–$C_4$-alkyloxy, each of which is optionally mono- or polysubstituted in the cycloalkyl moiety by identical or different substituents from the group consisting of:
$C_1$–$C_2$-alkyl, fluorine, chlorine., $C_1$–$C_2$-halogenoalkyl having 1 to 5 fluorine and/or chlorine atoms and $C_2$-alkenyl having 1 to 3 fluorine and/or chlorine atoms,
or phenyl which is optionally mono- or polysubstituted by identical or different substituents from the group consisting of:
halogen, $C_1$–$C_4$-alkyl, $C_1$–$C_4$-alkoxy, $C_1$–$C_2$-halogenoalkyl having 1 to 5 fluorine and/or chlorine atoms and $C_1$–$C_4$-halogenoalkoxy having one or more fluorine and/or chlorine atoms, or the radical —$NR^4$—$R^5$.

$R^4$ particularly preferably represents hydrogen or $C_1$–$C_2$-alkyl.

$R^5$ particularly preferably represents $C_1$–$C_4$-alkyl or phenyl or benzyl, each of which is optionally mono- or polysubstituted in the phenyl moiety by identical or different substituents from the group consisting of:
halogen, $C_1$–$C_2$-alkyl, $C_1$–$C_2$-halogenoalkyl having 1 to 5 fluorine and/or chlorine atoms and $C_1$–$C_2$-halogenoalkoxy having 1 to 5 fluorine and/or chlorine atoms,
or the radical —$C(R^6R^7)$—$C(R)$=$NOR^9$.

$R^6$ particularly preferably represents hydrogen or $C_1$–$C_3$-alkyl.

$R^7$ particularly preferably represents hydrogen or $C_1$–$C_3$-alkyl.

$R^8$ particularly preferably represents hydrogen, $C_1$–$C_3$-alkyl or $C_3$–$C_6$-cycloalkyl which is optionally substituted by one or two identical or different $C_1$–$C_3$-alkyl groups or halogens.

$R^9$ particularly preferably represents $C_1$–$C_4$-alkyl.

$Ar^1$ very particularly preferably represents phenyl which is optionally substituted by one to four, in particular one or two, identical or different substituents from the group consisting of:
F, Cl, Br, nitro, cyano, hydroxyl,
$C_1$–$C_4$-alkyl,
$C_1$–$C_2$-alkoxy,
$C_1$–$C_2$-alkylthio,
$C_1$–$C_2$-alkylsulphonyl,
$C_1$–$C_2$-alkyl which is substituted by one to five identical or different substituents from the group consisting of F and Cl,
$C_1$–$C_2$-alkoxy which is substituted by one to five identical or different substituents from the group consisting of F and Cl,
$C_1$–$C_2$-alkylthio which is substituted by one to five identical or different substituents from the group consisting of F and Cl,
$C_1$–$C_2$-alkylsulfonyl which is substituted by one to five identical or different substituents from the group consisting of F and Cl,
$C_1$–$C_2$-alkylamino,
di-($C_1$–$C_2$-alkyl)-amino, and phenyl which is substituted by one or two identical or different substituents from the group consisting of F, Cl, Br, $C_1$–$C_2$-alkyl, $C_1$–$C_2$-alkyl which is substituted by one to five identical or different F or Cl, $C_1$–$C_2$-alkoxy, $C_1$–$C_2$-alkoxy which is substituted by one to five identical or different substituents from the group consisting of F and Cl, $C_1$–$C_2$-alkylthio and $C_1$–$C_2$-alkylthio which is substituted by one to five identical or different substituents from the group consisting of F and Cl.

$Ar^2$ very particularly preferably represents phenyl which is optionally substituted by one to three, in particular one or two, identical or different substituents from the group consisting of:

F, Cl, Br,
$C_1$–$C_{18}$-alkyl,
$C_1$–$C_6$-alkoxy-$C_1$–$C_8$-alkyl,
$C_1$–$C_8$-alkoxy which is substituted by one to six identical or different substituents from the group consisting of F and Cl,
$C_1$–$C_2$-alkyl which is substituted by one to five identical or different substituents from the group consisting of F and Cl,
$C_1$–$C_{18}$-alkoxy and —$(OC_2H_4)_{1-3}$—O—$C_1$–$C_6$-alkyl,
$C_1$–$C_{15}$-alkylthio,
$C_1$–$C_8$-alkylthio which is substituted by one to six identical or different substituents from the group consisting of F and Cl,
tri-$C_1$–$C_6$-alkylsilyl,
phenyl-di-$C_1$–$C_6$-alkylsilyl,
3,4-difluoromethylenedioxo,
3,4-tetrafluoroethylenedioxo,
a benzo-fused group,
a fused $C_4$-alkanediyl group,
the groupings

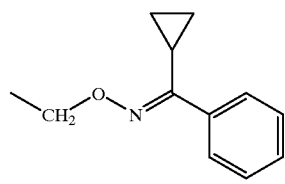

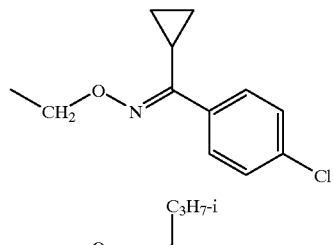

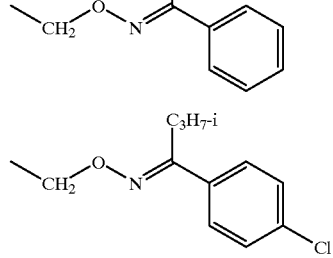

cyclohexyl or cyclohexyloxy, each of which is optionally substituted by $C_1$–$C_4$-alkyl, $C_1$–$C_4$-alkoxy, cyclohexyl or phenyl, pyridyloxy which is optionally substituted by one or two identical or different substituents from the group consisting of F,. Cl and $CF_3$, and phenyl which is optionally substituted by one or two identical or different $R^1$ radicals and/or optionally monosubstituted by —$OR^2$ groupings.

$R^1$ very particularly preferably represents fluorine, chlorine or bromine.

$R^2$ very particularly preferably represents hydrogen, or methyl, ethyl, propyl, butyl, pentyl, hexyl, or propenyl, butenyl, pentenyl, hexenyl, or propinyl, butinyl, pentinyl, or one the groups: —$CHF_2$, —$CF_2CHFCl$, —$CF_2CH_2F$, —$CF_2CHF_2$, —$CF_2CCl_3$, —$CF_2CHFCF_3$, —$CH_2CF_3$, —$CH_2CF_2CHF_2$, —$CH_2CF_2CF_3$, —$CF_2$—CHF—$CF_3$, or one of the cycloalkyl groupings:

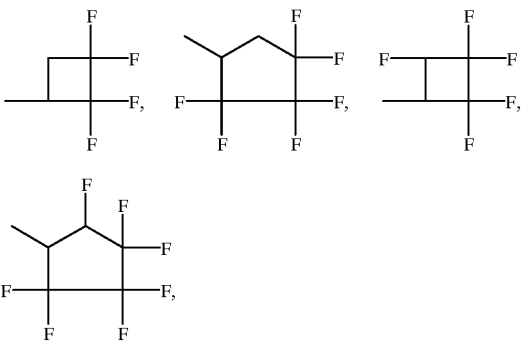

or one of the cycloalkenyl groupings:

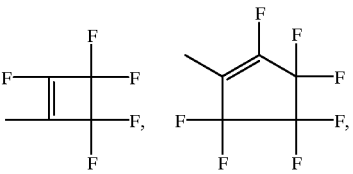

or one of the cycloalkylalkyl groupings:

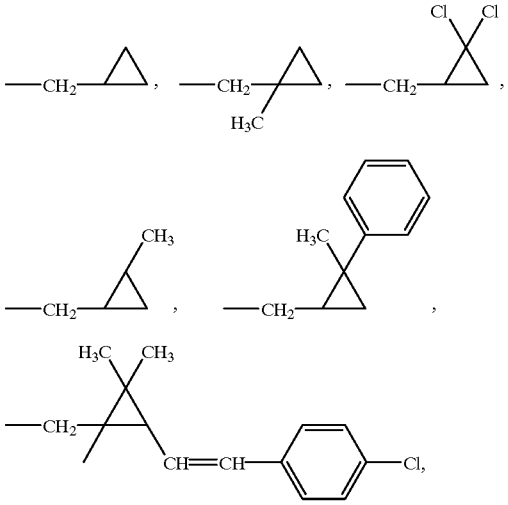

-continued

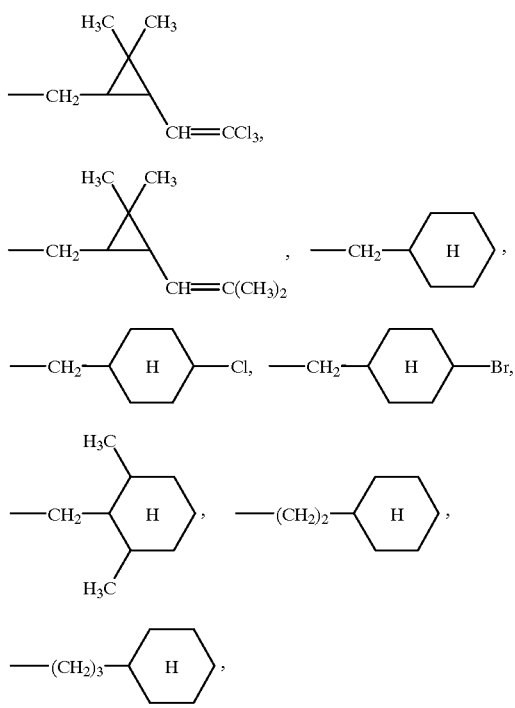

or one of the cycloalkenylalkyl groupings:

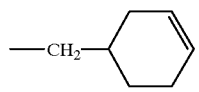

or one of the phenylalkyl groupings:

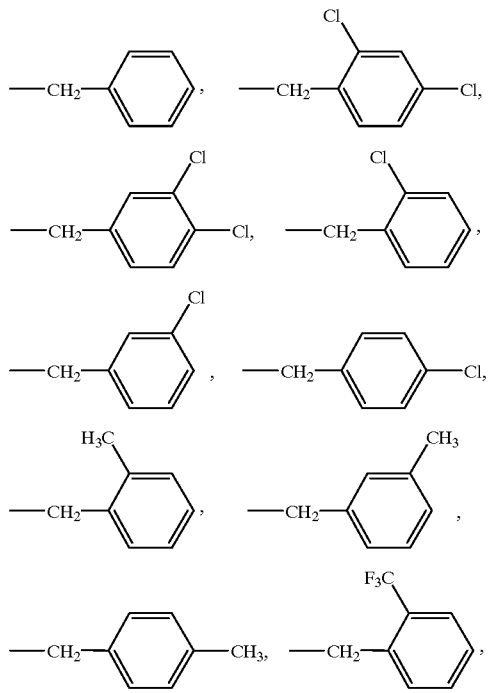

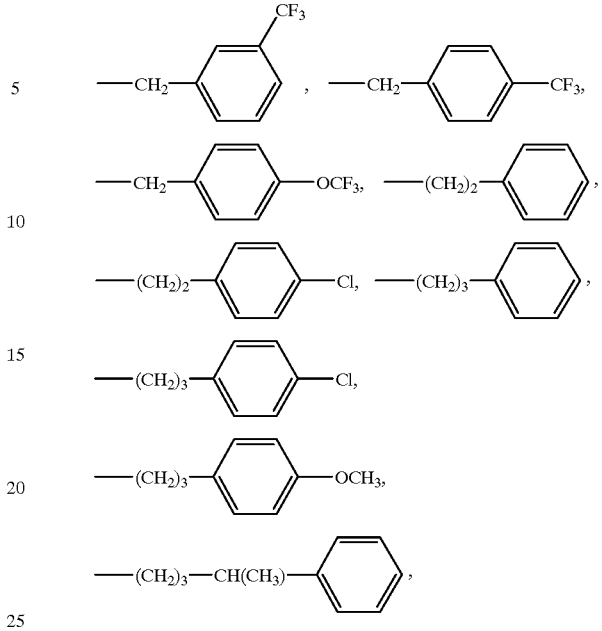

or the radical —COR³.

R³ very particularly preferably represents methyl, ethyl, propyl, or methoxy, ethoxy, propoxy, butoxy, or cyclopropyl, cyclohexyl, or cyclohexyloxy, or phenyl, 2-chlorophenyl, 3-chlorophenyl, 2,6-difluorophenyl, 2-trifluoromethoxyphenyl, 4-trifluoromethoxyphenyl, 2,4-dichlorophenyl, 3,4-dichlorophenyl, or the radical —NR⁴R⁵.

R⁴ very particularly preferably represents hydrogen.

R⁵ very particularly preferably represents methyl, ethyl or phenyl which is optionally monosubstituted by chlorine or represents the radical —C(R⁶R⁷)—C(R⁸)—NOR⁹.

R⁶ very particularly preferably represents hydrogen, methyl or ethyl.

R⁷ very particularly preferably represents hydrogen, methyl or ethyl.

R⁸ very particularly preferably represents hydrogen, methyl, ethyl or cyclopropyl, cyclopentyl or cyclohexyl, each of which is optionally substituted by one or two identical or different substituents from the group consisting of methyl, ethyl, i-propyl, fluorine, chlorine or bromine.

R⁹ very particularly preferably represents methyl, ethyl, n- or i-propyl.

The hydrocarbon radicals mentioned above in connection with the definition of the compounds according to the invention, such as alkyl or alkenyl, can—even in connection with hetero atoms, such as alkoxy—be in each case straight-chain or branched as far as this is possible.

The abovementioned general or preferred definitions of radicals or illustrations can be combined with each other as desired, that is to say combinations between the respective general and preferred ranges are also possible. They apply both to the end products and to the corresponding precursors and intermediates.

Preference according to the invention is given to the compounds of the formula (I) which contain a combination of the meanings mentioned above as being preferred (preferable).

Particular preference according to the invention is given to the compounds of the formula (I) which contain a combination of the meanings mentioned above as being particularly preferred.

Very particular preference according to the invention is given to the compounds of the formula (I) which contain a combination of the meanings mentioned above as being very particularly preferred.

Preference is given to compounds of the formula (IA)

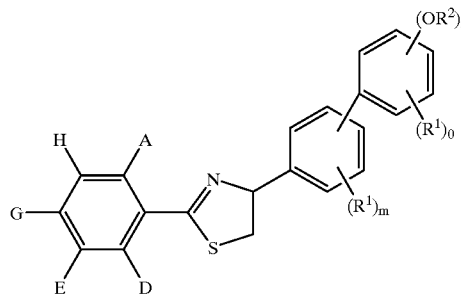
(IA)

in which

A, D, E, G and H represent the phenyl substituents mentioned above as being preferred, particularly preferred and very particularly preferred for $Ar^1$, in particular where A represents hydrogen, fluorine, chlorine, bromine, methyl, methoxy, trifluoromethoxy, methylthio or methylsulfonyl, D represents hydrogen, methyl, methoxy, fluorine or chlorine, E represents hydrogen, fluorine or chlorine, G represents hydrogen, fluorine, chlorine, bromine, methyl, t-butyl, trifluoromethoxy, trifluoromethylthio or dimethylamino and H represents hydrogen, fluorine, chlorine, methyl or methoxy, $R^1$ and $R^2$ each have the meanings given above as being preferred, particularly preferred and very particularly preferred, n is 0 or 1 and m and o each are independently of one another 0, 1 or 2.

Preference is further given to compounds of the formula (IB)

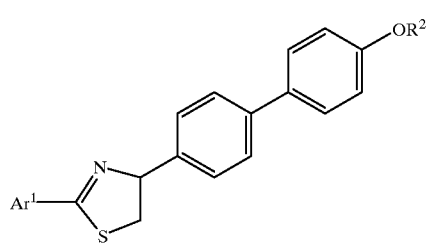
(IB)

in which $Ar^1$ represents the phenyl radicals below:

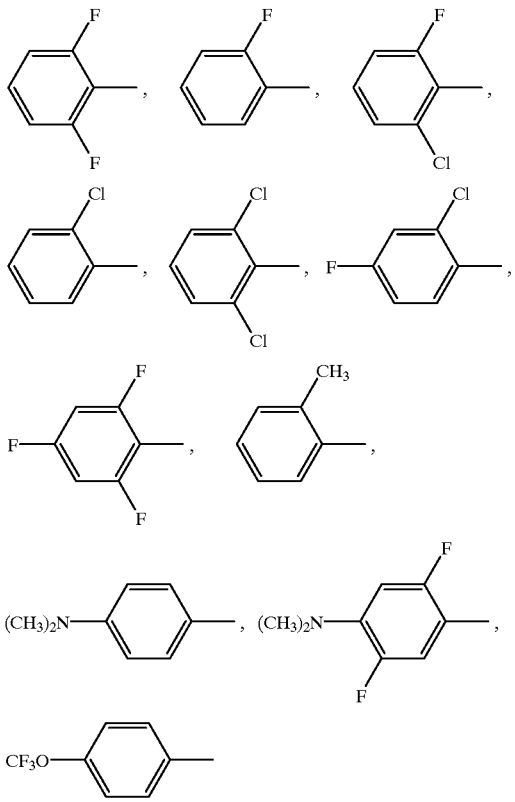

and $R^2$ has the meanings given above as being preferred, particularly preferred and very particularly preferred excluding alkyl, representing in particular halogenoalkyl or in particular halogen.

Besides the preparation examples, specific examples of the compounds of the formula (I)

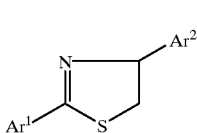
(I)

include:

| $Ar^1$ | $Ar^2$ |
|---|---|
| 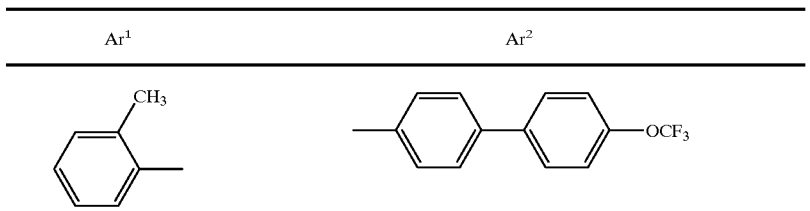 | |

-continued
| Ar¹ | Ar² |
|---|---|
| 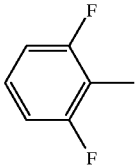 | 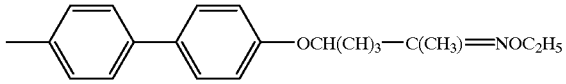 |
| 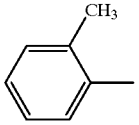 | 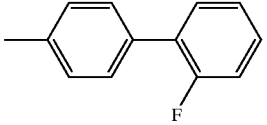 |
| 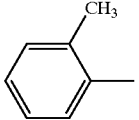 | 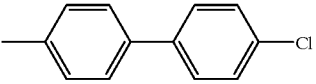 |
| 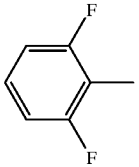 | 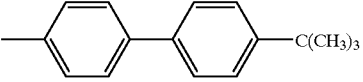 |
| 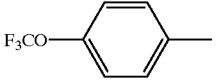 | 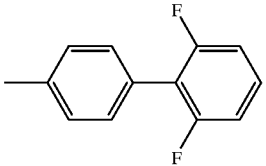 |
| 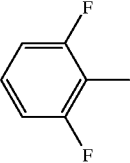 | 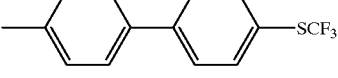 |
| 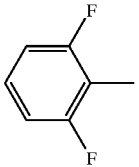 | 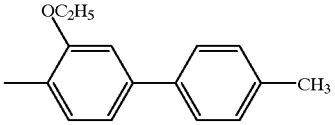 |
| 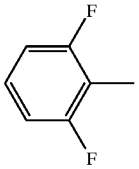 | 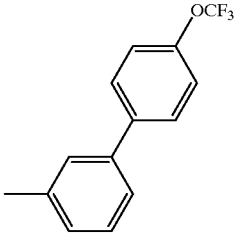 |

If process (a) is carried out using for example 2-(2,6-difluorophenyl)-4-(4-trifluoromethoxybiphenyl-4-yl)-2-oxazoline as starting material and phosphorus pentasulphide as sulphurizing agent, then the reaction of the process according to the invention may be illustrated by the following scheme:

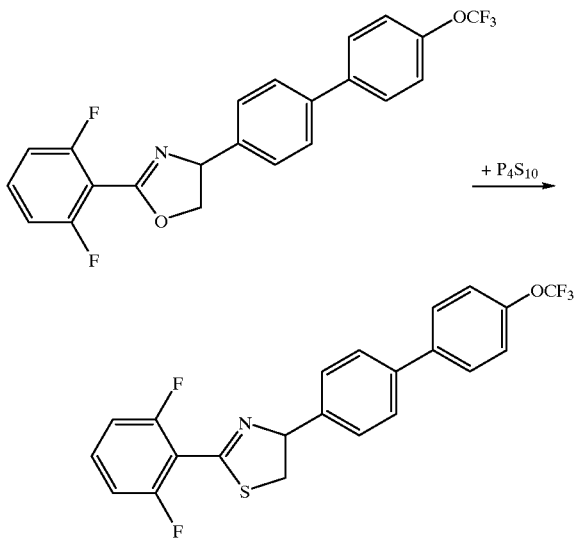

If process (b) is carried out using for example 2-(2-chlorophenyl)-4-bromophenyl-2-thiazoline and 4-(1-difluoro-2-difluoro-eth-1-yl-oxy)-phenylboronic acid as starting materials, then the reaction of the process according to the invention may be illustrated by the following scheme:

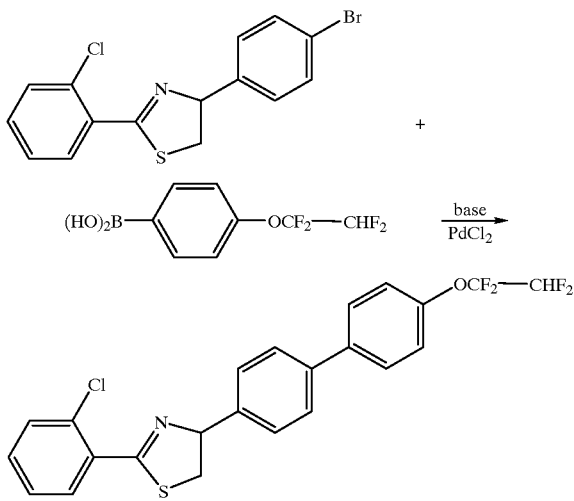

The oxazolines required as starting materials for carrying out the process (a) according to the invention are defined in a general way by the formula (II).

The oxazolines of the formula (II) are known (cf. for example EP-A-0 345 775, EP-A-0 432 661, WO-A 95/04726 or WO-A 95/19350) or they are the subject-matter of our own, still unpublished applications (cf. German Patent Applications 4 428 536 dated Dec. 08, 1994 and 4 435 716 dated Jun. 10, 1994) and/or can be obtained by the processes mentioned therein in a conventional and known manner.

The thiazolines required as starting materials for carrying out the process (b) according to the invention are defined in a general way by the formula (Ia).

Ph represents bromo-, iodo- or chlorophenyl which can be substituted by one or two identical or different substituents, in which case preferred, particularly preferred or very particularly preferred substituents are the radicals already specified above in connection with the description of the compounds of the formula (I) as preferred, particularly preferred or very particularly preferred for $R^1$.

The thiazolines of the formula (Ia) are compounds according to the invention obtainable by employing process (a).

The boronic acids also required as starting materials for carrying out the process (b) according to the invention are defined in a general way by the formula (III). In the formula (III), $Ph^1$ represents phenyl which is optionally substituted by one to three, preferably one or two, identical or different $R^1$ and/or $-OR^2$, $R^1$ and $R^2$ having preferably, particularly preferably or very particularly preferably those meanings already specified above, in connection with the description of the compounds of the formula (I), as preferred, particularly preferred or very particularly preferred for these substituents.

The boronic acids of the formula (III) are generally known compounds of organic chemistry and/or can be obtained by generally known methods.

Preferred sulphurizing agents for carrying out the process (a) according to the invention are: phosphorus pentasulphide or Lawesson's Reagent [2,4-bis(4-methoxyphenyl)-1,3,2,4-dithiadiphosphetane-2,4-dithione].

Preferred diluents for carrying out the process (a) according to the invention are hydrocarbons, such as toluene, xylene, tetralin, hexane or cyclohexane.

Reaction temperatures may be varied over a relatively wide range in the practice of the process (a) according to the invention. Generally, the reaction is carried out at temperatures between 0° C. and 200° C., preferably between 20° C. and 150° C.

In the practice of process (a) according to the invention, generally between 1 and 3 mol, preferably between 1 and 2 mol, of sulphurizing agent are employed per mole of oxazoline of the formula (II). Work-up is carried out using customary methods.

Suitable diluents for carrying out process (b) according to the invention are all organic solvents inert under the reaction conditions given. If appropriate, they can be employed in a mixture with water. Preferably used are hydrocarbons, such as toluene, xylene, tetralin, hexane and cyclohexane, halogenated hydrocarbons, such as methylene chloride, chloroform, chlorobenzene and o-dichlorobenzene, alcohols, such as methanol, ethanol, glycol, the isomeric propanols, butanols and pentanols, ethers, such as diethyl ether, diisopropyl ether, dimethoxyethane, tetrahydrofuran and dioxane, nitriles, such as acetonitrile or butyronitrile, amides such as dimethylformamide, sulphoxides such as dimethyl sulphide, and sulpholane.

Suitable bases for carrying out the process (b) according to the invention are all customary acid acceptors. Preference is given to using tertiary amines, such as triethylamine, pyridine, diazabicyclooctane (DABCO), diazabicycloundecene (DBU), diazabicyclononene (DBN) and N,N-dimethylaniline, further to alkaline earth metal oxides, such as magnesium oxide or calcium oxide, and also alkali metal carbonates and alkaline earth metal carbonates and alkali metal hydrogen carbonates, such as sodium carbonate, potassium carbonate, calcium carbonate and sodium hydrogen carbonate, alkali metal hydroxides, such as sodium hydroxide or potassium hydroxide, and also alkoxides, such as sodium ethoxide or potassium tert-butoxide.

If appropriate, the process (b) according to the invention is carried out in the presence of a catalyst. Suitable catalysts are for example: tetrakis(triphenylphosphine)palladium; palladium-II acetate/tri(o-tolyl)phosphine; palladium-II chloride, -II acetate/triphenylphosphine; bis(triphenylphosphine)palladium-II chloride; and Pd/C/triphenylphosphine.

Reaction temperatures may be varied over a relatively wide range in the practice of the process (b) according to the invention. Generally, the reaction is carried out at temperatures between 0° C. and 150° C., preferably between 0° C. and 100° C., or at the boiling point of the solvent used.

In the practice of process (b) according to the invention, generally between 1 and 3 mol, preferably between 1 and 1.5 mol, of boronic acid of the formula (III) and, if appropriate, between 0.01 and 0.2 mol, preferably between 0.05 and 0.1 mol, of catalyst are employed per mole of thiazoline of the formula (Ia), the catalyst being preferably charged initially and the thiazoline being added under a stream of inert gas, such as, for example, a stream of argon. Work-up is carried out by customary methods.

The active compounds are suitable for combating animal pests, in particular insects, arachnids and nematodes, encountered in agriculture, in forestry, in the protection of stored products and of materials, and in the hygiene field, and have good plant tolerance and favourable toxicity to warm-blooded animals. They may preferably be employed as crop protection agents. They are active against normally sensitive and resistant species and against all or some stages of development. The abovementioned pests include:

From the order of the Isopoda, for example, *Oniscus asellus, Armadillidium vulgare* and *Porcellio scaber.*

From the order of the Diplopoda, for example, *Blaniulus guttulatus.*

From the order of the Chilopoda, for example, *Geophilus carpophagus* and Scutigera spec.

From the order of the Symphyla, for example, *Scutigerella immaculata.*

From the order of the Thysanura, for example, *Lepisma saccharina.*

From the order of the Collembola, for example, *Onychiurus armatus.*

From the order of the Orthoptera, for example, *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria.*

From the order of the Dermaptera, for example, *Forficula auricularia.*

From the order of the Isoptera, for example, Reticulitermes spp.

From the order of the Anoplura, for example, *Pediculus humanus corporis,* Haematopinus spp. and Linognathus spp.

From the order of the Mallophaga, for example, Trichodectes spp. and Damalinea spp.

From the order of the Thysanoptera, for example, *Hercinothrips femoralis* and *Thrips tabaci.*

From the order of the Heteroptera, for example, Eurygaster spp., *Dysdercus intermedius, Piesma quadrata, Cimex lectularius, Rhodnius prolixus* and Triatoma spp.

From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Aphis pomi, Eriosoma lanigerum, Hyalopterus arundinis, Phylloxera vastatrix,* Pemphigus spp., *Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.

From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Spodoptera exigua, Mamestra brassicae, Panolis flammea, Spodoptera litura,* Spodoptera spp., *Trichoplusia ni, Carpocapsa pomonella,* Pieris spp., Chilo spp., *Pyrausta nubilalis, Ephestia kuehniella, Galleria mellonella, Tineola bisselliella, Tinea pellionella, Hofnannophila pseudospretella, Cacoecia podana, Capua reticulana, Choristoneura fumiferana, Clysia ambiguella, Homona magnanima* and *Tortrix viridana.*

From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica.*

From the order of the Hymenoptera, for example, Diprion spp., Hoplocampa spp., Lasius spp., *Monomorium pharaonis* and Vespa spp.

From the order of the Diptera, for example, Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa.*

From the order of the Siphonaptera, for example, *Xenopsylla cheopis* and Ceratophyllus spp.

From the order of the Arachnida, for example, *Latrodectus mactans.*

From the order of the Acarina, for example, *Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp., Tetranychus spp.

The phytoparasitic nematodes include, for example, Pratylenchus spp., *Radopholus similis, Ditylenchus dipsaci, Tylenchulus semipenetrans,* Heterodera spp., Globodera spp., Meloidogyne spp., Apelenchoides spp., Longidorus spp., Xiphinema spp., Trichodorus spp.

The compounds of the formula (I) according to the invention in particular have an excellent insecticidal and acaricidal action.

They can be used particularly successfully for controlling plant-damaging insects and mites.

They have a very strong action for example against mustard beetle larvae (*Phaedon cochleariae*), caterpillars of the diamondback moth (*Plutella maculipennis*), caterpillars of the owlet moth (*Spodoptera frugiperda*), aphids (*Myzus persicae*) and also against the spider mite (*Tetranychus urticae*) and the fruit tree red spider mite (*Panonychus ulmi*).

The active compounds can be converted to the customary formulations, such as solutions, emulsions, wettable powders, suspensions, powders, dusting agents, pastes, soluble powders, granules, suspension emulsion concentrates, natural and synthetic materials impregnated with active compound and very fine capsules in polymeric substances.

These formulations are produced in a known manner, for example by mixing the active compounds with extenders, that is liquid solvents and/or solid carriers, optionally with the use of surface-active agents, that is emulsifying agents and/or dispersing agents and/or foam-forming agents.

In the case of the use of water as an extender, organic solvents can, for example, also be used as auxiliary solvents. Suitable liquid solvents are essentially: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water.

Suitable solid carriers are for example ammonium salts and ground natural minerals, such as kaolins, clays, talc, chalk, quartz, attapulgite, montmorillonite or diatomaceous earth, and ground synthetic minerals, such as highly disperse silica, alumina and silicates; suitable solid carriers for granules are: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; suitable emulsifying and/or foam-forming agents are: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as protein hydrolysis products; suitable dispersing agents are: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compound according to the invention can be present in its commercially available formulations and in the use forms, prepared from these formulations, as a mixture with other active compounds, such as insecticides, attractants, sterilizing agents, bactericides, acaricides, nematicides, fungicides, growth-regulating substances or herbicides. The insecticides include, for example, phosphates, carbamates, carboxylates, chlorinated hydrocarbons, phenylureas and substances produced by microorganisms, inter alia.

Examples of particularly advantageous components are the following:

Fungicides:

2-aminobutane; 2-anilino-4methyl-6-cyclopropylpyrimidine; 2',6'-dibromo-2-methyl-4'-trifluoromethoxy-4'-trifluoro-methyl-1,3-thiazole-5-carboxanilide; 2,6-dichloro-N-(4-trifluoromethylbenzyl)-benzamide; (E)-2-methoxyimino-N-methyl-2-(2-phenoxyphenyl) acetamide; 8-hydroxyquinoline sulphate; methyl (E)-2-{2-[6-(2-cyanophenoxy)pyrimidin-4-yloxy]-phenyl}-3-methoxyacrylate; methyl (E)-methoximino[alpha-(o-tolyloxy)-o-tolyl]acetate; 2-phenylphenol (OPP), aldimorph, ampropylfos, anilazine, azaconazole, benalaxyl, benodanil, benomyl, binapacryl, biphenyl, bitertanol, blasticidin-S, bromuconazole, bupirimate, buthiobate, calcium polysulphide, captafol, captan, carbendazim, carboxin, quinomethionate, chloroneb, chloropicrin, chlorothalonil, chlozolinate, cufraneb, cymoxanil, cyproconazole, cyprofuram, dichlorophen, diclobutrazol, diclofluanid, diclomezine, dicloran, diethofencarb, difenoconazole, dimethirimol, dimethomorph, diniconazole, dinocap, diphenylamine, dipyrithione, ditalimfos, dithianon, dodine, drazoxolon, edifenphos, epoxyconazole, ethirimol, etridiazole, fenarimol, fenbuconazole, fenfuram, fenitropan, fenpiclonil, fenpropidin, fenpropimorph, fentin acetate, fentin hydroxide, ferbam, ferimzone, fluazinam, fludioxonil, fluoromide, fluquinconazole, flusilazole, flusulphamide, flutolanil, flutriafol, folpet, fosetylaluminium, fthalide, fuberidazole, furalaxyl, furmecyclox, guazatine, hexachlorobenzene, hexaconazole, hymexazol, imazalil, imibenconazole, iminoctadine, iprobenfos (IBP), iprodione, isoprothiolane, kasugamycin, copper preparations such as: copper hydroxide, copper naphthenate, copper oxychloride, copper sulphate, copper oxide, oxine-copper and Bordeaux mixture, mancopper, mancozeb, maneb, mepanipyrim, mepronil, metalaxyl, metconazole, methasulfocarb, methfuroxam, metiram, metsulfovax, myclobutanil, nickel dimethyldithiocarbamate, nitrothal-isopropyl, nuarimol, ofurace, oxadixyl, oxamocarb, oxycarboxin, pefurazoate, penconazole, pencycuron, phosdiphen, phthalide, pimaricin, piperalin, polycarbamate, polyoxin, probenazole, prochloraz, procymidone, propamocarb, propiconazole, propineb, pyrazophos, pyrifenox, pyrimethanil, pyroquilon, quintozene (PCNB), sulphur and sulphur preparations, tebuconazole, tecloftalam, tecnazene, tetraconazole, thiabendazole, thicyofen, thiophanate-methyl, thiram, tolclofos-methyl, tolylfluanid, triadimefon, triadimenol, triazoxide, trichlarnide, tricyclazole, tridemorph, triflumizole, triforine, triticonazole, validamycin A, vinclozolin, zineb, ziram.

Bactericides:

bronopol, dichlorophen, nitrapyrin, nickel dimethyldithiocarbamate, kasugamycin, octhilinone, furancarboxylic acid, oxytetracycline, probenazole, streptomycin, tecloftalam, copper sulphate and other copper preparations.

Insecticides/Acaricides/Nematicides:

abamectin, AC 303 630, acephate, acrinathrin, alanycarb, aldicarb, alphamethrin, amitraz, avermectin, AZ 60541, azadirachtin, azinphos A, azinphos M, azocyclotin,

*Bacillus thuringiensis*, bendiocarb, benfuracarb, bensultap, beta-cyfluthrin, bifenthrin, BPMC, brofenprox, bromophos A, bufencarb, buprofezin, butocarboxim, butylpyridaben, cadusafos, carbaryl, carbofuran, carbophenothion, carbosulfan, cartap, CGA 157419, CGA 184699, chloethocarb, chlorethoxyfos, chlorfenvinphos, chlorfluazuron, chlormephos, chlorpyrifos, chlorpyrifos M, cis-resmethrin, clocythrin, clofentezine, cyanophos, cycloprothrin, cyfluthrin, cyhalothrin, cyhexatin, cypermethrin, cyromazine, deltamethrin, demeton M, demeton S, demeton-S-methyl, diafenthiuron, diazinon, dichlofenthion, dichlorvos, dicliphos, dicrotophos, diethion, diflubenzuron, dimethoate, dimethylvinphos, dioxathion, disulfoton, edifenphos, emamectin, esfenvalerate, ethiofencarb, ethion, ethofenprox, ethoprophos, etrimfos, fenamiphos, fenazaquin, fenbutatin oxide, fenitrothion, fenobucarb, fenothiocarb, fenoxycarb, fenpropathrin, fenpyrad, fenpyroximate, fenthion, fenvalerate, fipronil, fluazinam, flucycloxuron, flucythrinate, flufenoxuron, flufenprox, fluvalinate, fonofos, formothion, fosthiazate, fubfenprox, furathiocarb, HCH, heptenophos, hexaflumuron, hexythiazox, imidacloprid, iprobenfos, isazofos, isofenphos, isoprocarb, isoxathion, ivermectin, lambda-cyhalothrin, lufenuron, malathion, mecarbam, mevinphos, mesulphenphos, metaldehyde, methacrifos, methamidophos, methidathion, methiocarb, methomyl, metolcarb, milbemectin, monocrotophos, moxidectin, naled, NC 184, NI 25, nitenpyram, omethoate, oxamyl, oxydemeton M, oxydeprofos, parathion A, parathion M, permethrin, phenthoate, phorate, phosalone, phosmet, phosphamidon, phoxim, pirimicarb, pirimiphos M, pirimiphos A, profenofos, promecarb, propaphos, propoxur, prothiofos, prothoate, pymetrozine, pyrachlofos, pyridaphenthion, pyresmethrin, pyrethrum, pyridaben, pyrimidifen, pyriproxyfen, quinalphos,

RH 5992, salithion, sebufos, silafluofen, sulphotep, sulprofos, tebufenozide, tebufenpyrad, tebupirimifos, teflubenzuron, tefluthrin, temephos, terbam, terbufos, tetrachlorvinphos, thiafenox, thiodicarb, thiofanox, thiometon, thionazin, thuringiensin, tralomethrin, triarathene, triazophos, triazuron, trichlorfon, triflumuron, trimethacarb, vamidothion, XMC, xylylcarb, YI 5301/5302, zetamethrin.

A mixture with other known active ingredients, such as herbicides, or with fertilizers and growth-regulators is also possible.

The active compounds according to the invention can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

When used against hygiene pests and pests of stored products, the active compounds are distinguished by an excellent residual action on wood and clay as well as a good stability to alkali on limed substrates.

The active compounds according to the invention are not only active against plant, hygiene and stored-product pests, but also, in the veterinary medicine sector, against animal parasites (ectoparasites), such as ixodid ticks, argasid ticks, scab mites, trombiculid mites, flies (stinging and sucking), parasitic fly larvae, lice, hair lice, bird lice and fleas. These parasites include:

From the order of the Anoplurida, for example, Haematopinus spp., Linognathus spp., Pediculus spp., Phtirus spp., Solenopotes spp.

From the order of the Mallophagida and the sub-orders Amblycerina and Ischnocerina, for example, Trimenopon spp., Menopon spp., Trinoton spp., Bovicola spp., Werneckiella spp., Lepikentron spp., Damalina spp., Trichodectes spp., Felicola spp.

From the order of the Diptera and the sub-orders Nematocerina and Brachycerina, for example, Aedes spp., Anopheles spp., Culex spp., Simulium spp., Eusimulium spp., Phlebotomus spp., Lutzomyia spp., Culicoides spp., Chrysops spp., Hybomitra spp., Atylotus spp., Tabanus spp., Haematopota spp., Philipomyia spp., Braula spp., Musca spp., Hydrotaea spp., Stomoxys spp., Haematobia spp., Morellia spp., Fannia spp., Glossina spp., Calliphora spp., Lucilia spp., Chrysomyia spp., Wohlfahrtia spp., Sarcophaga spp., Oestrus spp., Hypoderma spp., Gasterophilus spp., Hippobosca spp., Lipoptena spp. and Melophagus spp.

From the order of the Siphonapterida, for example, Pulex spp., Ctenocephalides spp., Xenopyslla spp. and Ceratophyllus spp.

From the order of the Heteropterida, for example, Cimex spp., Triatoma spp., Rhodnius spp. and Panstrongylus spp.

From the order of the Blattarida, for example, *Blatta orientalis, Periplaneta americana, Blattela germanica* and Supella spp.

From the sub-class of the Acaria (Acarida) and the orders of the Meta- and Mesostigmata, for example, Argas spp., Ornithodorus spp., Otabius spp., Ixodes spp., Amblyomrma spp., Boophilus spp., Dermacentor spp., Haemaphysalis spp., Hyalomma spp., Rhipicephalus spp., Dermanyssus spp., Raillietia spp., Pneumonyssus spp., Sternostoma spp. and Varroa spp.

From the order of the Actinedida (Prostigmata) and Acaridida (Astigmata), for example, Acarapis spp., Cheyletiella spp., Ornithocheyletia spp., Myobia spp., Psorergates spp., Demodex spp., Trombicula spp., Listrophorus spp., Acarus spp., Tyrophagus spp., Caloglyphus spp., Hypodectes spp., Pterolichus spp., Psoroptes spp., Chorioptes spp., Otodectes spp., Sarcoptes spp., Notoedres spp., Knemidocoptes spp., Cytodites spp. and Laminosioptes spp.

For example, they show a good retarding activity against Lucilla cuprina fly larvae and against Ctenocephalides felis flea eggs.

In addition, they affect the moulting of polyphagous ticks such as *Amblyoma vanegatum*.

The active compounds of the formula (I) according to the invention are also suitable for controlling arthropods which attack agricultural livestock, such as, for example, cattle, sheep, goats, horses, pigs, donkeys, camels, buffaloes, rabbits, chickens, turkeys, ducks, geese, honey bees, other domestic animals, such as, for example, dogs, cats, caged birds, aquarium fish, and so-called experimental animals, such as, for example, hamsters, guinea-pigs, rats and mice. By controlling these arthropods, it is intended to reduce deaths and decreased performances (in meat, milk, wool, hides, eggs, honey and the like), so that more economical and simpler animal keeping is made possible by using the active compounds according to the invention.

In the veterinary sector, the active compounds according to the invention are used in a known manner by enteral administration, for example in the form of tablets, capsules, drinks, drenches, granules, pastes, boluses, the feed-through method, suppositories, by parenteral administration, such as, for example, by means of injections (intramuscular, subcutaneous, intravenous, intraperitoneal and the like), implants, by nasal administration, by dermal administration, for example in the form of dipping or bathing, spraying, pouring-on and spotting-on, washing, dusting, and with the aid of shaped articles which comprise active compound, such as collars, ear tags, tail marks, limb bands, halters, marking devices and the like.

When administered to livestock, poultry, domestic animals and the like, the active compounds of the formula (I) can be used as formulations (for example powders, emulsions, flowables) which comprise the active compounds in an amount of 1 to 80% by weight, either directly or after dilution by a factor of 100 to 10 000, or they may be used in the form of a chemical bath.

Furthermore, it has been found that the compounds of the formula (I) according to the invention have a potent insecticidal action against insects which destroy industrial materials.

The following insects may be mentioned by way of example and as being preferred, but without any limitation:

Beetles, such as *Hylotrupes bajulus, Chlorophorus pilosis, Anobium punctatum, Xestobium rufovillosum, Ptilinus pecticornis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthes rugicollis*, Xyleborus spec., *Tryptodendron* spec., *Apate monachus, Bostrychus capucins, Heterobostrychus brunneus*, Sinoxylon spec., *Dinoderus minutus*.

Dernapterans, such as *Sirex juvencus, Urocerus gigas, Urocerus gigas taignus, Urocerus augur*.

Termites, such as *Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis, Coptotermes formosanus*.

Bristletails, such as *Lepisma saccharina*.

Industrial materials are to be understood as meaning, in the present context, non-live materials, such as, preferably, synthetic materials, glues, sizes, paper and board, leather, wood and timber products, and paint.

The materials to be very particularly preferably protected against attack by insects are wood and timber products.

Wood and timber products which can be protected by the composition according to the invention or mixtures comprising such a composition are to be understood as meaning, for example, construction timber, wooden beams, railway sleepers, bridge components, jetties, wooden vehicles, boxes, pallets, containers, telephone poles, wood lagging, windows and doors made of wood, plywood, particle board, joiner's articles, or wood products which, quite generally, are used in the construction of houses or in joinery.

The active compounds can be used as such, in the form of concentrates or generally customary formulations, such as powders, granules, solutions, suspensions, emulsions or pastes.

The formulations mentioned can be prepared in a manner known per se, for example by mixing the active compounds with at least one solvent or diluent, emulsifier, dispersant and/or binder or fixative, water repellent, if appropriate desiccants and UV stabilizers and, if appropriate, colorants and pigments and other processing auxiliaries.

The insecticidal compositions or concentrates used for the protection of wood and wooden materials comprise the active compound according to the invention at a concentration of 0.0001 to 95% by weight, in particular 0.001 to 60% by weight.

The amount of the compositions or concentrates employed depends on the species and the occurrence of the insects and on the medium. The optimum rate of application can be determined upon use in each case by test series. However, in general, it suffices to employ 0.0001 to 20% by weight, preferably 0.001 to 10% by weight, of the active compound, based on the material to be protected.

The solvent and/or diluent used is an organochemical solvent or solvent mixture and/or an oily or oil-type organochemical solvent or solvent mixture of low volatility and/or a polar organochemical solvent or solvent mixture and/or water and, if appropriate, an emulsifier and/or wetting agent.

Organochemical solvents which are preferably employed are oily or oil-like solvents having an evaporation number of above 35 and a flashpoint of above 30° C., preferably above 45° C. Substances which are used as such oily and oil-like solvents which have low volatility and are insoluble in water are suitable mineral oils or their aromatic fractions, or mineral-oil-containing solvent mixtures, preferably white spirit, petroleum and/or alkylbenzene.

Substances which are advantageously used are mineral oils with a boiling range of 170 to 220° C., white spirit with a boiling range of 170 to 220° C., spindle oil with a boiling range of 250 to 350° C., petroleum or aromatics of boiling range 160 to 280° C., essence of terpentine and the like.

In a preferred embodiment, liquid aliphatic hydrocarbons with a boiling range of 180 to 210° C. or high-boiling mixtures of aromatic and aliphatic hydrocarbons with a boiling range of 180 to 220° C. and/or spindle oil and/or monochloronaphthalene, preferably α-monochloronaphthalene, are used.

The organic oily or oil-like solvents of low volatility and having an evaporation number of above 35 and a flashpoint of above 30° C., preferably above 45° C., can be partially replaced by organochemical solvents of high or medium volatility, with the proviso that the solvent mixture also has an evaporation number of above 35 and a flashpoint of above 30° C., preferably above 45° C., and that the insecticide/fungicide mixture is soluble or emulsifiable in this solvent mixture.

In a preferred embodiment, part of the organochemical solvent or solvent mixture is replaced by an aliphatic polar organochemical solvent or solvent mixture. Substances which are preferably used are aliphatic organochemical solvents having hydroxyl and/or ester and/or ether groups, such as, for example, glycol ether, esters and the like.

The organochemical binders used within the scope of the present invention are the synthetic resins and/or binding drying oils which are known per se and can be diluted with water and/or are soluble or dispersible or emulsifiable in the organochemical solvents employed, in particular binders composed of, or comprising, an acrylate resin, a vinyl resin, for example polyvinyl acetate, polyester resin, polycondensation or polyaddition resin, polyurethane resin, alkyd resin or modified alkyd resin, phenol resin, hydrocarbon resin, such as indene/coumarone resin, silicone resin, drying vegetable and/or drying oils and/or physically drying binders based on a natural and/or synthetic resin.

The artificial resin used as the binder can be employed in the form of an emulsion, dispersion or solution. Up to 10% by weight of bitumen or bituminous substances can also be used as binder. In addition, colorants, pigments, water repellents, odour-masking substances and inhibitors or anti-corrosives known per se and the like can also be employed.

The composition or the concentrate preferably comprises, in accordance with the invention, at least one alkyd resin or modified alkyd resin and/or a drying vegetable oil as the organochemical binder. Preferably used according to the invention are alkyd resins with an oil content of over 45% by weight, preferably 50 to 68% by weight.

All or some of the abovementioned binder can be replaced by a fixative (mixture) or a plasticizer (mixture). These additives are intended to prevent volatilization of the active compounds and crystallization or precipitation. They preferably replace 0.01 to 30% of the binder (based on 100% of binder employed).

The plasticizers are from the chemical classes of the phthalic esters, such as dibutyl phthalate, dioctyl phthalate or benzylbutyl phthalate, the phosphoric esters, such as tributyl phosphate, the adipic esters, such as di-(2-ethylhexyl) adipate, the stearates, such as butyl stearate or amyl stearate, the oleates, such as butyl oleate, the glycerol ethers or relatively high-molecular-weight glycol ethers, glycerol esters and p-toluene-sulphonic esters.

Fixatives are chemically based on polyvinyl alkyl ethers, such as, for example, polyvinyl methyl ether, or ketones, such as benzophenone or ethylenebenzophenone.

Particularly suitable as a solvent or diluent is also water, if appropriate as a mixture with one or more of the abovementioned organochemical solvents or diluents, emulsifiers and dispersants.

Particularly effective protection of wood is achieved by large-scale industrial impregnation processes, for example vacuum, double-vacuum or pressure processes.

If appropriate, the ready-to-use compositions can additionally comprise other insecticides and, if appropriate, additionally one or more fungicides.

Suitable additional components which may be admixed are, preferably, the insecticides and fingicides mentioned in WO 94/29 268. The compounds mentioned in that document are expressly incorporated into the present application by reference.

Very particularly preferred components which may be admixed are insecticides, such as chlorpyrifos, phoxim, silafluofin, alphamethrin, cyfluthrin, cypermethrin, deltamethrin, permethrin, imidacloprid, NI-25, flufenoxuron, hexaflumuron and triflumuron, and fungicides, such as epoxyconazole, hexaconazole, azaconazole, propiconazole, tebuconazole, cyproconazole, metconazole, imazalil, dichlofluanid, tolylfluanid, 3-iodo-2-propinylbutyl carbamate, N-octyl-isothiazolin-3-one and 4,5-dichloro-N-octylisothiazolin-3-one.

The preparation and the use of the active compounds according to the invention can be seen from the examples which follow.

PREPARATION EXAMPLES

Example 1

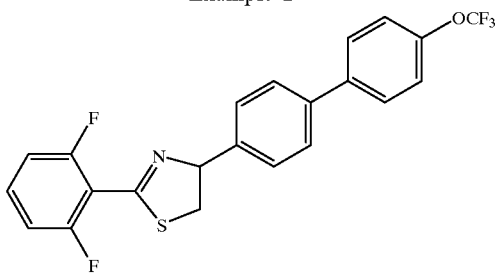

(Process (a))

2.8 g (0.0067 mol) of 2-(2,6-difluorophenyl)4-(4-trifluoromethoxybiphenyl-4-yl)-2-oxazoline and 6 g (0.013 mol) of phosphorus pentasulphide are stirred at 130° C. for 18 hours. After cooling, the reaction mixture is admixed with 100 ml of ice-water and, after addition of 40 ml of 45% strength aqueous sodium hydroxide solution, stirred for 1 hour. The mixture is then extracted several times with 100 ml of dichloromethane each. The combined organic phases are washed repeatedly with dilute aqueous sodium hydroxide solution (until a clear solution is obtained), dried over magnesium sulphate and concentrated under reduced pressure.

1.8 g (62% of theory) of 2-(2,6-difluorophenyl)-4-(4-trifluoromethoxybiphenyl-4-yl)-2-thiazoline of melting point 85–86° C. are obtained.

Using a method similar to Example 1 or following the general preparation instructions, the following compounds of the formula (I) are obtained:

(I)

| Ex. No. | Ar$^1$ | Ar$^2$ | Physical data |
|---|---|---|---|
| 2 | 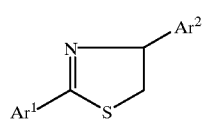 | | m.p.: 109–10° C. |

-continued

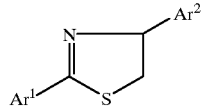

| Ex. No. | Ar¹ | Ar² | Physical data |
|---|---|---|---|
| 3 | 2,3-difluorophenyl | 4'-(OCF₂CHClF)-biphenyl-4-yl | ¹H-NMR (ppm in CDCl₃) 3.46(1H); 3.95(1H); 5.82(1H); 6.35–6.23(1H); 7.74–6.97(aromatic H) |
| 4 | 2,3-difluorophenyl | 4'-(OCF₂—CHF—CF₃)-biphenyl-4-yl | m.p.: 80–83° C. |
| 5 | 2-fluorophenyl | 4'-(OCF₃)-biphenyl-4-yl | m.p.: 65–66° C. |
| 6 | 2-chlorophenyl | 4'-(OCF₂—CHF—CF₃)-biphenyl-4-yl | ¹H-NMR (ppm in CDCl₃) 3.43(1H); 3.92(1H); 5.79(1H); 5.11–4.94(1H); 7.73–7.29(aromatic H) |

Use Examples

Example A

Phaedon larvae test

Solvent: 7 parts by weight of dimethylformamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of the active compound of the desired concentration and are infested with mustard beetle larvae (*Phaedon cochleariae*) while the leaves are still moist.

After the specified period of time, the destruction in % is determined. 100% means that all the beetle larvae have been killed; 0% means that none of the beetle larvae have been killed.

In this test, a destruction of 100% was brought about, after 7 days, for example by the compounds of Preparation Examples 1, 2, 3 and 4 at an exemplary active compound concentration of 0.1%.

Example B

Plutella test

Solvent: 7 parts by weight of dimethylformamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of the active compound of the desired concentration and are infested with caterpillars of the diamondback moth (*Plutella maculipennis*) while the leaves are still moist.

After the specified period of time, the destruction in % is determined. 100% means that all the caterpillars have been killed; 0% means that none of the caterpillars have been killed.

In this test, a destruction of 100% was brought about, after 7 days, for example by the compounds of Preparation Examples 1, 2, 3, 4 and 5 at an exemplary active compound concentration of 0.1%.

Example C

Spodoptera test

Solvent: 7 parts by weight of dimethylformamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of the active compound of the desired concentration and are infested with caterpillars of the owlet moth (*Spodoptera frugiperda*) while the leaves are still moist.

After the specified period of time, the action in % is determined. 100% means that all the caterpillars have been killed; 0% means that none of the caterpillars have been killed.

In this test, a destruction of 100% was brought about, after 7 days, for example by the compounds of Preparation Examples 1, 3, 4 and 5 at an exemplary active compound concentration of 0.1%.

Example D

Myzus test

Solvent: 7 parts by weight of dimethylformamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) heavily infested with green aphids (*Myzus persicae*) are dipped into the preparation of the active compound of the desired concentration and placed into a plastic dish.

After the specified period of time, the destruction in % is determined. 100% means that all the aphids have been killed; 0% means that none of the aphids have been killed.

In this test, a destruction of 80% or 98% was brought about, after 6 days, for example by the compounds of Preparation Examples 1 and 3, respectively, at an exemplary active compound concentration of 0.1%.

Example E

Tetranychus test (OP resistant/dip treatment)

Solvent: 3 parts by weight of dimethylformamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with emulsifier-containing water to the desired concentration.

Bean plants (*Phaseolus vulgaris*) heavily infested by all stages of the spider mite (*Tetranychus urticae*) are dipped into a preparation of the active compound of the desired concentration.

After the specified period of time, the action in % is determined. 100% means that all the spider mites have been killed; 0% means that none of the spider mites have been killed.

In this test, a destruction of 98% was brought about, after 7 days, for example by the compounds of Preparation Examples 1, 2, 3, 4 and 5 at an exemplary active compound concentration of 0.01%.

Example F

Panonychus test

Solvent: 3 parts by weight of dimethylformamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with emulsifier-containing water to the desired concentration.

Plum trees (*Prunus domestica*), about 30 cm in height and heavily infected by all stages of the fruit tree red spider mite (*Panonychus ulmi*), are sprayed with a preparation of the active compound of the desired concentration.

After the specified period of time, the action in % is determined. 100% means that all the spider mites have been killed; 0% means that none of the spider mites have been killed.

In this test, a destruction of 100% was brought about, after 7 days, for example by the compounds of Preparation Examples 1, 2 and 3 at an exemplary active compound concentration of 0.02%.

Example G

Blowfly larvae test/development-inhibitory action

Test animals: Lucilia cuprina larvae

Emulsifier: 35 parts by weight of ethylene glycol monomethyl ether 35 parts by weight of nonylphenol polyglycol ether To produce a suitable preparation of active compound, 3 parts by weight of active compound are mixed with 7 parts by weight of the abovementioned mixture, and the resulting emulsion concentrate is diluted with water to the desired concentration.

For each individual concentration, 30 to 50 larvae are introduced into a test tube which contains 1 cm$^3$ of horse meat. 500 µl of the dilution to be tested are pipetted onto this horse meat. The test tubes are placed in plastic beakers whose bottom is covered with sea sand, and kept in a climatized room (26° C.±1.5° C., 70%±10% relative humidity). The activity is examined (larvicidal action) after 24 hours and again after 48 hours. After emergence of the larvae (about 72 h), the test tubes are removed and perforated plastic lids are fitted to the beakers. After 1.5 times the development time (hatching of the control flies), the hatched flies and the pupae/cocoons are counted.

The activity criterion is the incidence of death in treated larvae after 48 h (larvicidal effect), or the inhibition of the hatching of adults from pupae or the inhibition of pupa formation. The criterion for the in-vitro activity of a substance is the inhibition of the development of the flies, or a development standstill before the adult stage. 100% larvicidal action means that all the larvae have been killed after 48 hours. 100% development-inhibitory action means that no adult flies have hatched.

In this test, an activity of 100% was shown, for example, by the compounds of Preparation Examples 1, 2 and 3 at an exemplary active compound concentration of 1000 ppm.

Example H

Test with cat fleas/development-inhibitory action

Test animals: Ctenocephalides felis (all stages: eggs, larvae, pupae and adults)

Solvent: 35 parts by weight of ethylene glycol monomethyl ether

Emulsifier: 35 parts by weight of nonylphenol polyglycol ether

To produce a suitable preparation, 3 parts by weight of active compound are mixed with 7 parts by weight of the abovementioned solvent-emulsifier mixture, and the resulting emulsion concentrate is diluted with water to the desired concentration.

200 ml of this active compound preparation are added to 1.8 g of culture medium (blood meal medium: 125 parts of sea sand, 20 parts of rat food, 3 parts of blood meal, 2 parts of dry yeast) in disposable test tubes (Ø2.0 cm), homogenized and dried overnight. The medium is then charged with a spatula-tipful of sieved flea eggs (obtained from artificially infected cats).

For up to 1.5 times the development time of the control experiment, the activity of the active compound preparation is determined every 2 days by examining the experiments for flea development stages.

The criterion for the in-vitro activity of a substance is the inhibition of the development of the fleas, or a development standstill before the adult stage. 100% means that no adult fleas developed; 0% means that adult fleas hatched.

In this test, an activity of 100% was shown, for example, by the compound of Preparation Example 1 at an exemplary active compound concentration of 1000 ppm.

Example I

Ecdysis test on polyphagous tick nymphs

Test animals: Amblyomma variegatum ticks which have sucked themselves full

Solvent: 35 parts by weight of ethylene glycol monomethyl ether

Emulsifier: 35 parts by weight of nonylphenol polyglycol ether

To produce a suitable formulation, 3 parts by weight of active compound are mixed with 7 parts of the abovementioned solvent-emulsifier mixture, and the resulting emulsion concentrate is diluted with water to the concentration desired in each case.

10 nymphs which have sucked themselves full are immersed for 1 minute into the preparation of active compound to be tested. The animals are transferred to petri dishes (Ø9.5 cm) which are equipped with filter-paper discs and covered. After the nymphs have remained in a controlled-environment cabinet for 4 weeks, the ecdysis rate is determined.

100% means that none of the animals have undergone normal ecdysis; 0% means that all the animals have undergone normal ecdysis.

In this test, an activity of 100% was shown, for example, by the compound of Preparation Example 2 at an exemplary active compound concentration of 1000 ppm.

What is claimed is:
1. Compounds of the formula (IB)

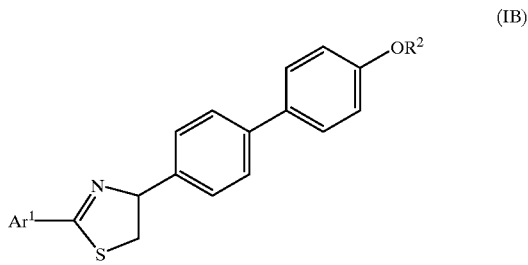

in which
$Ar^1$ represents the following phenyl radicals:

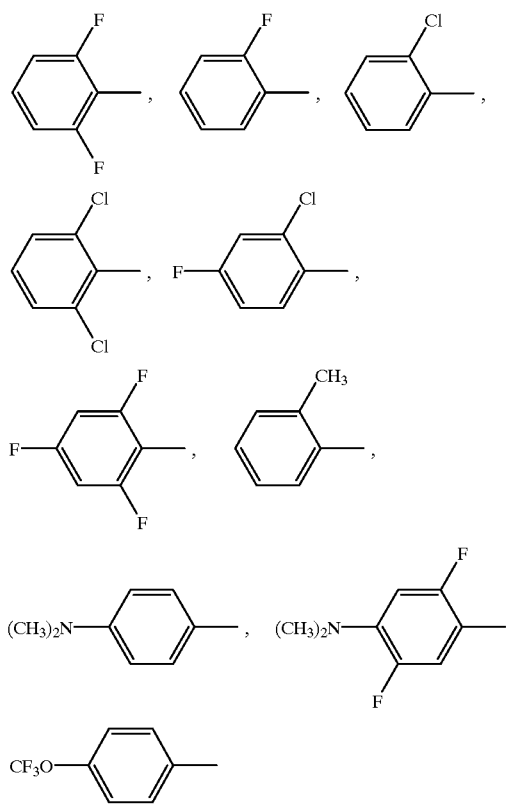

$R^2$ represents hydrogen, $C_{1-12}$-alkyl or $C_3$–$C_{12}$-alkenyl, or $C_3$–$C_{12}$-alkinyl, or $C_1$–$C_6$-halogenoalkyl having one or more fluorine and/or chlorine atoms, or $C_3$–$C_6$-cycloalkyl or $C_3$–$C_6$-cycloalkyl-$C_1$–$C_4$-alkyl, each of which is optionally mono- or polysubstituted in the cycloalkyl moiety by identical or different substituents from the group consisting of:
halogen, $C_1$–$C_4$-alkyl, $C_2$–$C_4$-alkenyl which is optionally mono- or polysubstituted by halogen, and phenyl or styryl, each of which is optionally mono- or polysubstituted, by halogen;
or represents $C_4$–$C_6$-cycloalkenyl or $C_4$–$C_6$-cycloalkenyl-$C_1$–$C_4$-alkyl, each of which is optionally mono- or polysubstituted by identical or different halogen and/or $C_1$–$C_4$-alkyl substituents;
or represents phenyl-$C_1$–$C_4$-alkyl or naphthylmethyl, each of which is optionally mono- or polysubstituted in the aryl moiety by identical or different substituents from the group consisting of:

halogen, $C_1$–$C_{12}$-alkyl, $C_1$–$C_{12}$-halogenoalkyl having one or more fluorine and/or chlorine atoms, $C_1$–$C_{12}$-alkoxy and $C_1$–$C_{12}$-halogenoalkoxy having one or more fluorine and/or chlorine atoms;

or represents the radical —$COR^3$ where $R^3$ represents $C_1$–$C_{12}$-alkyl, or $C_1$–$C_{12}$-alkoxy, or $C_3$–$C_{12}$-alkenyl, or $C_3$–$C_{12}$-alkenyloxy, or represents $C_3$–$C_6$-cycloalkyl, $C_3$–$C_{10}$-cycloalkyloxy or $C_3$–$C_{10}$-cycloalkyl-$C_1$–$C_6$-alkoxy, each of which is optionally mono- or polysubstituted in the cycloalkyl moiety by identical or different substituents from the group consisting of:

$C_1$–$C_4$-alkyl, halogen, $C_1$–$C_4$-halogenoalkyl having one or more fluorine and/or chlorine atoms and $C_2$–$C_4$-halogenoalkenyl having one or more fluorine and/or chlorine atoms;

or represents phenyl or naphthyl, each of which is optionally mono- or polysubstituted by identical or different substituents from the group consisting of:

halogen, $C_1$–$C_{12}$-alkyl, $C_1$–$C_{12}$-halogenoalkyl having one or more fluorine and/or chlorine atoms, $C_1$–$C_{12}$-alkoxy and $C_1$–$C_{12}$-halogenoalkoxy having one or more fluorine and/or chlorine atoms;

or represents the radical —$NR^4$—$R^5$ where $R^4$ represents hydrogen or $C_1$–$C_{12}$-alkyl and $R^5$ represents $C_1$–$C_{12}$-alkyl, $C_1$–$C_{12}$-halogenoalkyl having one or more fluorine and/or chlorine atoms, or $C_3$–$C_6$-cycloalkyl or $C_3$–$C_6$-cycloalkyl-$C_1$–$C_4$-alkyl, each of which is optionally mono- or polysubstituted in the cycloalkyl moiety by identical or different substituents from the group consisting of:

$C_1$–$C_4$-alkyl, halogen, $C_1$–$C_4$-halogenoalkyl having one or more fluorine and/or chlorine atoms and $C_2$–$C_4$-halogenoalkenyl having one or more fluorine and/or chlorine atoms;

or represents phenyl or phenyl-$C_1$–$C_6$-alkyl, each of which is optionally mono- or polysubstituted, by identical or different substituents from the group consisting of:

halogen, $C_1$–$C_{12}$-alkyl, $C_1$–$C_{12}$-halogenoalkyl having one or more fluorine and/or chlorine atoms, $C_1$–$C_{12}$-alkoxy and $C_1$–$C_{12}$-halogenoalkoxy having one or more fluorine and/or chlorine atoms;

or represents the radical —$C(R^6R^7)$—$C(R^8)$=$NOR^9$ where $R^6$ and $R^7$ are identical or different and represent hydrogen or $C_1$–$C_4$-alkyl, $R^8$ represents hydrogen, $C_1$–$C_4$-alkyl or $C_3$–$C_6$-cycloalkyl which is optionally mono-, di- or trisubstituted by identical or different substituents from the group consisting of $C_1$–$C_4$-alkyl, halogen or $C_1$–$C_4$-halogenoalkyl and $R^9$ represents $C_1$–$C_4$-alkyl, except the compounds:

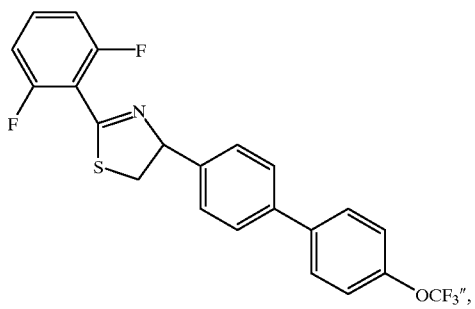

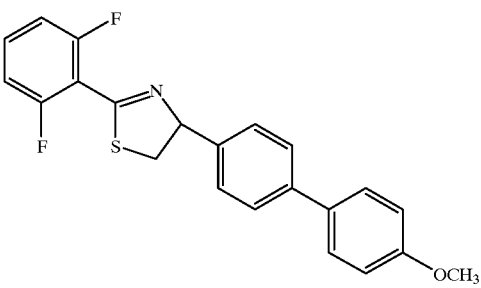

and

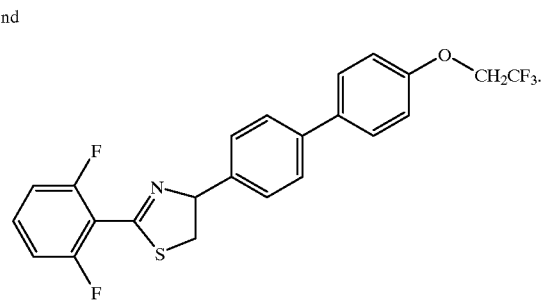

2. Compounds of the formula (IB) according to claim 1 in which $R^2$ represents halogenoalkyl.

3. Processes for preparing compounds of the formula (I),

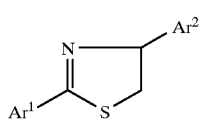
(I)

in which $Ar^1$ and $Ar^2$ each represent independently of one another optionally substituted phenyl;

said processes comprising a) reacting compounds of the formula (II)

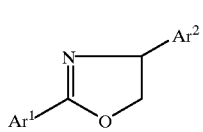
(II)

in which $Ar^1$ and $Ar^2$ each have the meanings above, with a sulphurizing agent, optionally in the presence of a diluent; or b) reacting compounds of the formula (Ia)

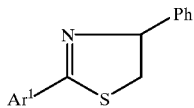
(Ia)

in which

Ar¹ has the meaning given above; and
Ph represents optionally substituted halogenophenyl;

with boronic acids of the formula (III)

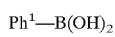 (III)

in which

Ph¹ represents optionally substituted phenyl;

in the presence of a base, optionally in the presence of a catalyst and in the presence of a diluent.

4. A pesticidal composition comprising a pesticidally effective amount of at least one compound according to claim 1 and an extender and/or surface active agent.

5. A method of combating pests comprising applying a pesticidally effective amount of at least one compound according to claim 1 to the pests and/or their habitat and/or to a location from which it is desired to exclude such pests.

6. A process for preparing a pesticidal composition according to claim 4 comprising mixing said compound with said extender and/or surface active agent.

7. A compound according to claim 1, which has the formula

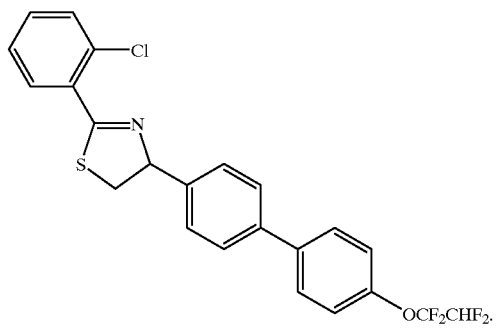

8. A compound according to claim 1, which has the following structure:

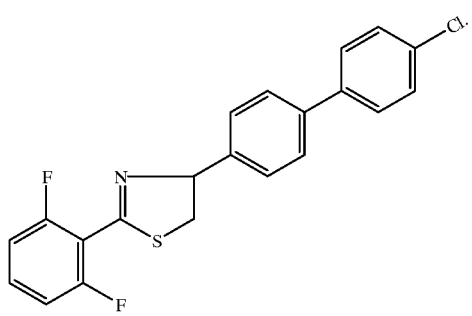

9. A compound according to claim 1, which has the following structure:

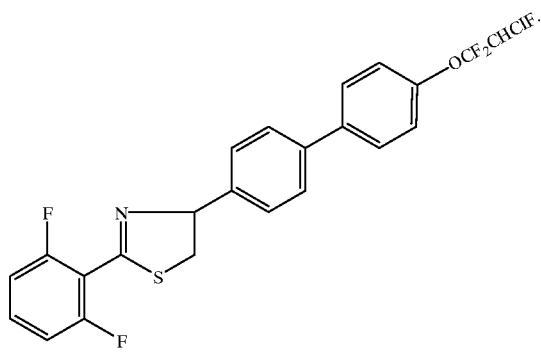

10. A compound according to claim 1, which has the following structure:

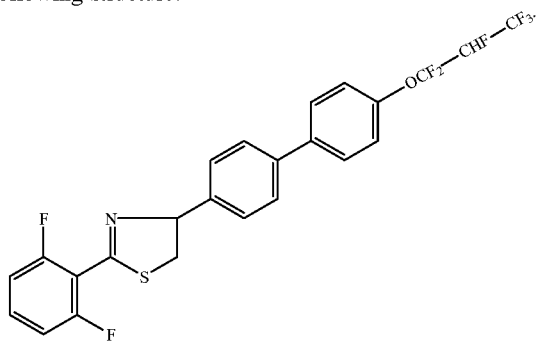

11. A compound according to claim 1, which has the following structure:

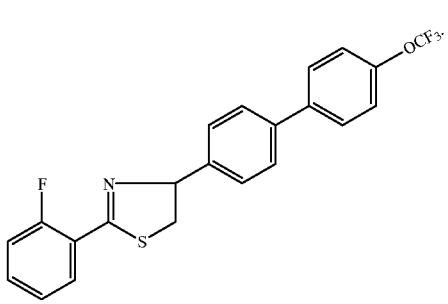

12. A compound according to claim 1, which has the following structure:

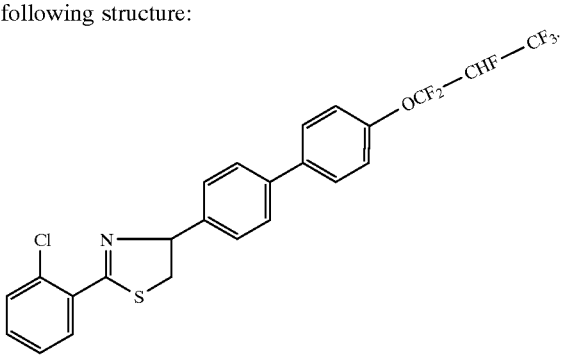

* * * * *

UNITED STATES PATENT AND TRADEMARK OFFICE
CERTIFICATE OF CORRECTION

PATENT NO.    : 6,255,328 B1
DATED         : July 3, 2001
INVENTOR(S)   : Bernd Alig et al.

It is certified that error appears in the above-identified patent and that said Letters Patent is hereby corrected as shown below:

<u>Title page,</u>
Item [56], References Cited, FOREIGN PATENT DOCUMENTS, add:
-- WO 96/22283   7/25/96   World --
OTHER PUBLICATIONS, add:   -- J. Chem. Soc. Perkin Trans. 1, 1997, --

Signed and Sealed this

Sixteenth Day of September, 2003

JAMES E. ROGAN
*Director of the United States Patent and Trademark Office*